United States Patent [19]

Levin

[11] Patent Number: 4,978,507

[45] Date of Patent: Dec. 18, 1990

[54] FLUID FLOW MANIFOLD FOR BLOT TYPE SCREENING APPARATUS

[76] Inventor: Andrew E. Levin, 145 Bishop Allen Dr., Cambridge, Mass. 02139

[21] Appl. No.: 200,135

[22] Filed: May 31, 1988

[51] Int. Cl.$^5$ .................. C12M 1/12; C12M 1/20; G01N 33/48

[52] U.S. Cl. .................. 422/100; 137/595; 222/479; 222/630; 422/101; 422/103; 435/293; 435/301

[58] Field of Search .............. 422/101, 103, 100; 435/293, 301; 137/595; 222/630, 479

[56] References Cited

U.S. PATENT DOCUMENTS 4,713,349 12/1987 Levin .................. 436/515
4,834,946  5/1989 Levin .................. 422/101

*Primary Examiner*—Robert J. Warden
*Assistant Examiner*—Jill Johnston
*Attorney, Agent, or Firm*—Harness, Dickey & Pierce

[57] ABSTRACT

A blot screening apparatus is formed of a plate having numerous, elongated, narrow, shallow, parallel, separated reaction channels formed in one surface. The channel openings are positioned over a treated membrane which reacts with fluids introduced into the various channels. An elongated, narrow, groove-like socket, formed in the opposite plate surface, overlaps and extends transversely over each of the opposite and portions of the channels. Holes formed in the plate communicate the opposite ends of each channel with the base of its overlapping socket so that fluid samples may be separately introduced into each channel through its holes. Manifold plugs that are shaped to closely fit within the sockets are removably positioned in, and frictionally sealed against, the walls of the sockets, but are spaced from their adjacent socket bases. Each plug has a fluid flow passage for flowing a fluid simultaneously through the manifold plug to its socket base, through all of the base holes and channels, and out of the opposite channel holes, socket base and plug for simultaneously filling and draining all of the channels.

13 Claims, 1 Drawing Sheet

U.S. Patent
Dec. 18, 1990
4,978,507
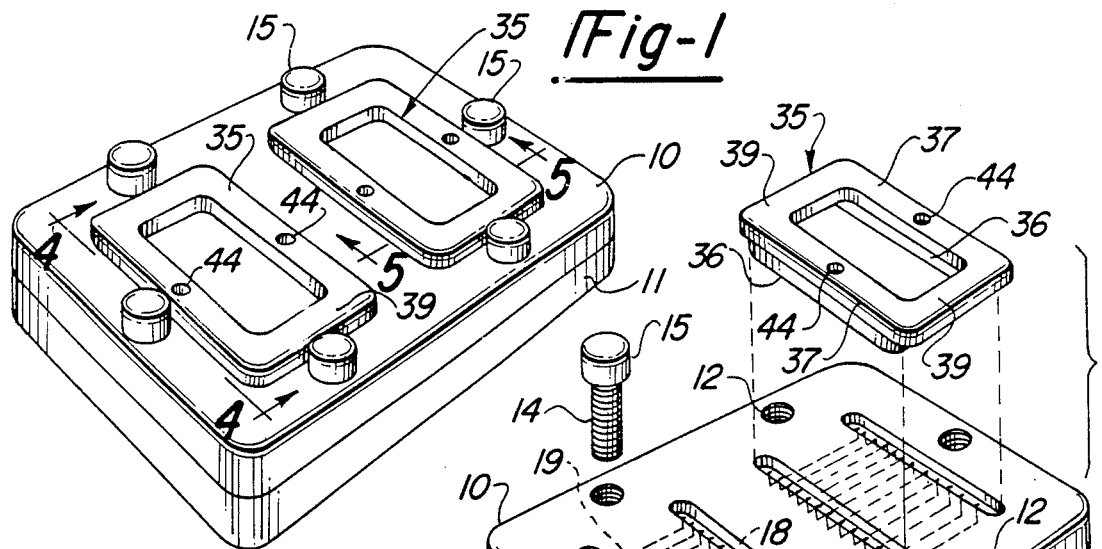
Fig-1
Fig-2
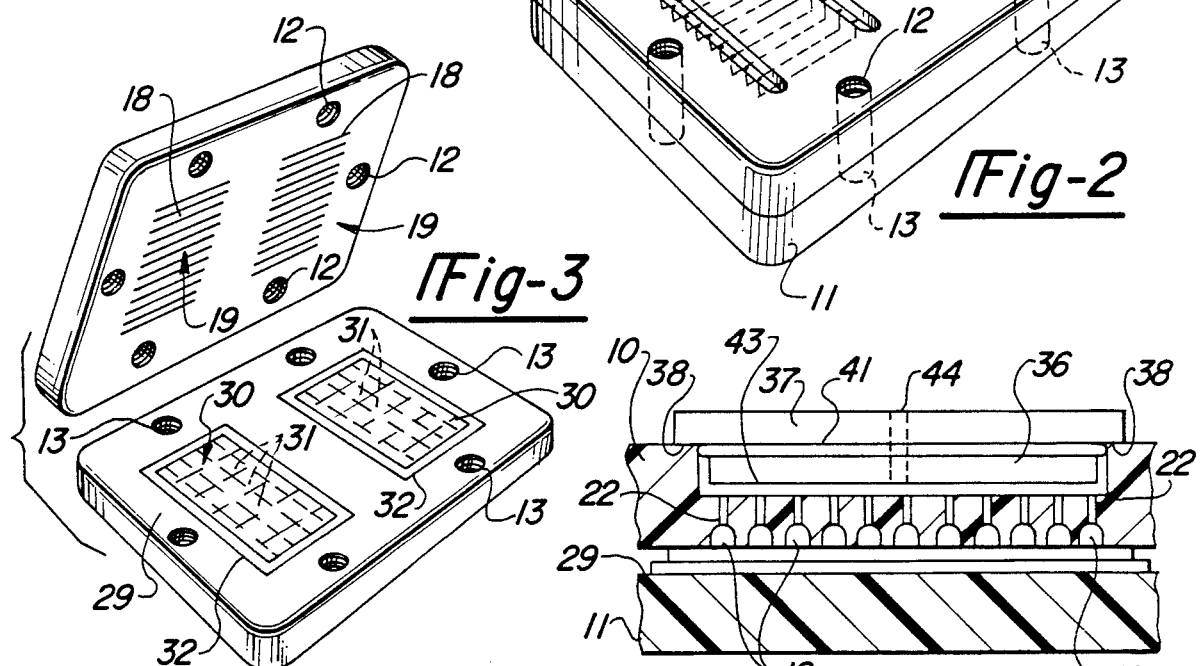
Fig-3
Fig-4
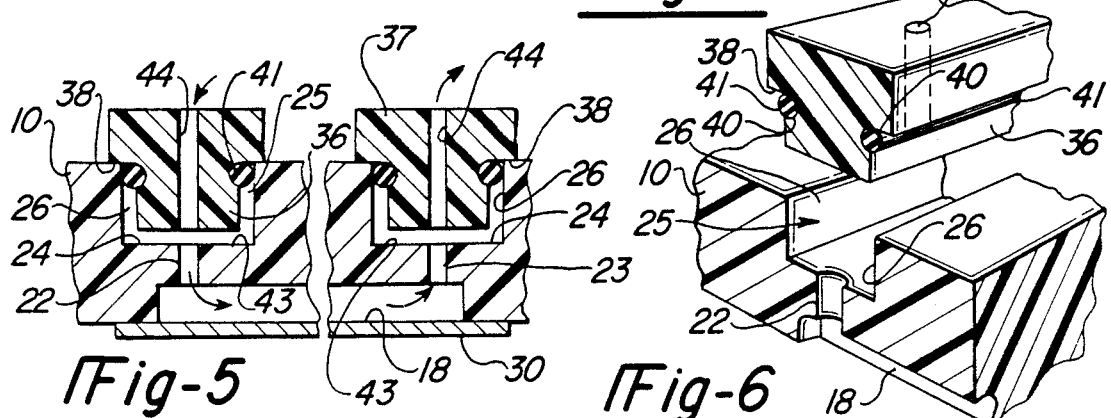
Fig-5
Fig-6

FLUID FLOW MANIFOLD FOR BLOT TYPE SCREENING APPARATUS

BACKGROUND OF INVENTION

This invention relates to an improved manifold useful in washing or flushing the reaction channels in an apparatus used in laboratories for screening certain types of solutions. The improved manifold relates to the type of apparatus disclosed in my prior application for U.S. Pat. Ser. No. 07/011,291, now U.S. Pat. No. 4,834,946, filed Feb. 5, 1987, for "An Apparatus For Blot Screening Numerous, Small Volume, Antibody Solutions." A similar type of apparatus is also disclosed in my prior U.S. Pat. No. 4,713,349, issued Dec. 15, 1987, for a "Template For Simultaneously Screening of Several Antibodies and Method of Using the Same."

A known method, which is used to screen samples of different antibody solutions by the Western Blotting procedure, generally involves reacting the test solutions with proteins or antigens which have been immobilized on a transfer membrane. Visually observable markings, resulting from the reactions, appear on the membrane. These markings can be used for a screening analysis. To facilitate the procedure, and to reduce the time required for this type of analysis, microliter-size samples of different test solutions are introduced into channels in a plate for simultaneous contact with different parts of a treated transfer membrane. After reactions occur, it is necessary to flush the channels in order to rinse unbonded or unreacted materials therefrom. Also, for some tests it may be necessary to apply a single reactive fluid into all of the channels at about the same time. Initially, the channels are loaded individually or in small groups with the small samples for testing. Thus, there is a need for means for introducing and removing a single fluid, either for rinse or reaction purposes, simultaneously through all of the channels, while still permitting loading each channel separately.

By way of further background, the Western Blot procedure with which this apparatus is primarily concerned utilizes a thin membrane having bands of protein that were applied and separated through a gel electrophoresis procedure. During the blot procedure, the membrane is incubated with a primary antibody. Following incubation, unbound portions of the primary antibody are washed away. Then, the membrane may be incubated with a secondary or tracer antibody which is subjected to a washing step for removing unbound secondary antibody materials. Lastly, the membrane may be incubated with a color-generating substrate to produce visually observable antibody sites in the form of color bands or markings. These are used to determine analysis results.

The membranes utilized are commonly made of paper-like nitrocellulose sheets which carry proteins that have been electroblotted from polyacrylamide gels. The gels can include a single sample that is electrophoresed across the entire gel for use for screening a number of antibodies against the same antigen pattern. Alternatively, antibodies may be screened against different antigens electrophoresed in separate vertical lanes on the same gel.

In this type of screening, a relatively large number of separate rows or stripes of the sample solutions under assay are applied upon a single transfer membrane to produce side-by-side observable readings of the test results. The transfer membranes have a relatively large number of different bands of immobilized antigens located along the length of the membranes. Thus, the stripes of antibody solutions are applied transversely to the numerous bands. Observable test results occur at various locations along the lengths of the stripes where they intersect with the different bands. This provides the side-by-side comparisons of antibody blotting profiles.

This laboratory screening procedure may be conducted with an apparatus such as that disclosed in my above-mentioned application. That apparatus utilizes a test plate having a surface in which a large number of shallow, narrow, elongated channels are formed. The surface is applied against the test membrane, with the channels arranged transversely of the bands formed on the membrane. Test solution materials are introduced in each of the channels for contact with different parts of the single membrane. Since a large number of tests are conducted at the same time and with the same membrane, this procedure considerably reduces the overall time and expense needed for conducting such tests.

The apparatus described in my prior application includes a device which enables simultaneous introduction of a single fluid, such as a water rinse, through all of the channels. Although effective, it is desirable to provide a simpler device, which can be more rapidly applied and removed, so as to further reduce the amount of time and effort needed to conduct this laboratory testing procedure.

SUMMARY OF INVENTION

This invention contemplates an improved manifold system for temporary use with a screening apparatus plate having numerous, parallel channels, formed in one surface, which overlay a treated, transfer membrane against which test solutions are to be reacted. Fill and drain holes extend from the channels to the opposite surface of the plate so that different test solutions may be introduced, through the holes, into each of the respective channels. A pair of groove-like, depressed sockets, formed in the plate surface opposite to the channeled surface transversely overlay the opposite ends of the aligned, parallel channels. Thus, the channel fill and drain holes extend from the opposite ends of each channel into the bases of the respective sockets. Manifolds, shaped like elongated, narrow plugs which closely fit into each of the sockets, are inserted in the sockets when it is desired to fill or drain all of the channels simultaneously. These plugs have central openings for flowing fluid to the socket bases and, consequently, introducing or removing fluids simultaneously through all of the holes. Otherwise, the manifolds are removed from the sockets, so that each of the channel holes is exposed for separately introducing test fluids into the respective channels.

The manifold plugs are frictionally held within the sockets by means of a suitable resilient ring extending around each of them. The ring, which is shaped like an elongated O-ring, is compressed against the adjacent socket wall portion to seal the plug against the socket wall. Because the sockets are deeper than the plugs, a gap or space is located between the inner end of the manifold plug and the base of the socket to form a chamber-like area into which the channel holes open. Thus, when the area is filled with a fluid, such as water, the fluid flows through all the holes into the channels. Conversely, during rising or flushing of the channels, the rinse liquid flows out of the channels, through the holes, and into the area between the opposite socket base and end plug. By using a suitable vacuum evacuation pump, such as is commonly found in laboratories, the exiting fluid may be drained through a drain opening in the plug.

The manifolds may be manually applied or removed simply by pushing the plug like portions into the respective sockets so that O-rings compress and seal laterally outwardly against the walls defining the sockets. Thus, the manifolds can be rapidly applied and removed and yet will remain in place for as long as necessary.

An object of this invention is to provide a detachable manifold through which a continous stream of fluid may be passed for simultaneously entering or exiting numerous test channels. This enables rapid rinsing of all of the channels and also enables rapid application of other reaction solutions, such as secondary antibodies, to all of the channels simultaneously.

Another object of this invention is to provide a temporary means for simultaneously introducing and removing fluid in an apparatus having a large number of channels, such as 28 to 45 channels, arranged side-by-side. This permits rapid washing or flushing of all of the channels by supplying water through one manifold plug and removing it from the opposite plug. The liquid may be introduced under pressure or removed by vacuum, or both. For example, the liquid may be poured in a large syringe barrel acting as a funnel and removed by a conventional laboratory vacuum pump.

A further object of this invention is to provide a manifold system utilizing two separate plug-like parts which are rigidly interconnected so as to form a unitary or integral, rigid manifold that may be rapidly pushed into, or pulled out of, the inlet and outlet sockets formed in the apparatus plate using one hand, without tools or separate fastening devices.

Still a further object of this invention is to provide a simple, manually insertable and removable, temporary manifold for filling and emptying a multiple-channel screen apparatus plate that requires no separate fastening means or sealing means, and which is liquid-tight even if hurriedly positioned relative to the plate.

These and other objects and advantages of this invention will become apparent upon reading the following description, of which the attached drawings form a part.

DESCRIPTION OF DRAWINGS

FIG. 1 is a perspective view of the screening apparatus with the manifolds temporarily installed.

FIG. 2 is a perspective view showing the manifolds removed and the plate fastening screws removed.

FIG. 3 is a perspective view showing the underside of the upper, screening plate and the upper face of the base plate.

FIG. 4 is an enlarged, fragmentary, cross-sectional view of the assembled parts with the manifold in position and taken in the direction or arrows 4—4 of FIG. 1.

FIG. 5 is an enlarged, fragmentary, cross-sectional view taken in the direction of arrows 4—4 of FIG. 1.

FIG. 6 is an enlarged, perspective, fragmentary, cross-sectional view showing the manifold in position for insertion into the socket formed in the upper plate.

DETAILED DESCRIPTION

As shown in the drawings, the apparatus includes an upper, screening plate 10 and a lower, base plate 11. The screening plate is provided with unthreaded holes 12 which are aligned with threaded holes 13 formed in the base plate. Large screws 14, having manually graspable head 15, are extended through the aligned holes for tightly fastening the plates together.

The lower surface of the screening plate 10 is provided with numerous parallel channels 18 which are arranged in a pair of spaced apart arrays 19. While the number and sizes of the channels may vary, depending upon the intended testing purposes, typically the channels are shallow, very narrow, elongated and arranged substantially parallel. For example, the widths of the channels may run in the range of 1.5 to 4.0 millimeters with their lengths running from approximately 5.5 to 13 centimeters. Preferably, the lengths are many times greater than the widths. As an example, the channels may have depths of roughly in the range of 0.040 inches so that their volumes are in the microliter range. For example, a 1.5 millimeter wide, 5.5 centimeter long channel may have a volume of about 50 microliters, while a 4.0 millimeter width, 5.5 centimeter length channel has a volume of approximately 100 microliters. A similar 4.0 millimeter width, 13 centimeter in length channel may have a volume of close to 250 microliters. Thus, the amount of test liquid needed for filling the channels is intended to be minute.

While the drawings illustrate a pair of arrays of channels, the channels may be arranged in a single array upon the plate. The number of channels may vary considerably. For example, an array may have 16 channels that are 4.0 millimeters in width or 28 channels that are 1.5 millimeters in width, etc.

Each of the channels has an inlet hole 22 and an outlet hole 23. These extend upwardly from locations that are near the opposite ends of the channels. The holes open into the base 24 of a groove-like socket 25. A socket is arranged transversely of the channels at each end of the channels. These elongated, groove-like sockets have continuous walls 26 defining their sides and ends.

The inlet and outlet holes are aligned either in straight rows or in rows in which alternate holes may be slightly offset relative to each other so that they are substantially straight rows. Thus, each of the sockets overlays a row of inlet or outlet holes. In use, the user fills each of the channels through one or the other of its holes. This can be accomplished using a suitable commercially available automatic pipetting device or a multiple pipetting device used for handling multiple streams of microliter size quantities of liquids.

The upper surface 29 of the base plate 11 acts as a support for the treated membrane 30. The membrane may be formed with a number of different bands of immobilized antigens 31 or the like. The membrane is preferably placed upon a thin, resilient cushion sheet 32 which may be on the order of thickness of between about 0.015–0.040 inches in thickness. Thus, it is similar in thickness to a relatively thick sheet of paper. Preferably, the cushion sheet is formed of a resilient, foam plastic material, such as a closed cell polyethylene foam. One suitable example of such material is "Plastazote P-4053," sold by BXL Plastic, Ltd. of Surrey, England. This is a spongy material which can be compressed and which will tend to bulge between lines of compression. Any similar spongy or resilient material having essentially the same characteristics can be used.

When the cushion support sheet 32 is compressed by the plate lands, that is, the parts of the screening plate lower surface which are located between the channels, the cushion sheet material located between the compression lines will bulge upwardly towards the channels. That causes the membrane to bulge into the channels. Using a cushion material which has a density of roughly 2.8 pounds per cubic feet, that resilient bulging tends to reduce the volume of the channels by about 20 percent. That is, the bulging of stripes of the treated membrane 30 directly upwardly into the channels closes the channels and simultaneously reduces their volumes by about 20 percent. In addition, the bulging increases the amount of the membrane within each of the channels.

The transfer membrane 30 is of a size to overlay the array of channels or at least to overlay the number of channels that are to be used for any particular test. The membranes that are commonly used are made of nitrocellulose, nonwoven paper-like sheets upon which proteins or other antigens have been immobilized. The membrane is prepared through known procedures. Typically, the membrane includes either the same or different antigens which are applied and immobilized after prior separation by gel electrophoresis. Alternatively, antigens may be applied to and immobilized on, the membrane in separate stripes without prior electrophoretic separation. The differnt bands 31 are schematically shown in dotted lines on the treated membrane 30 isllustrated in FIG. 3.

In conducting a test, a cushion sheet 32, with the treated membrane 30 located upon it, is placed upon the upper surface 29 of the base plate 11. Then, the upper screening plate 10 is positioned upon the base plate so that the array of channels covers the membrane. The two plates are fastened together by manually inserting and fastening the screw 14. Then, the test solutions are introduced through the holes 22 into each of the channels.

After the incubation period required for the reactions between the test solutions and the membrane, the unbound antibody materials may be washed away. This is accomplished by manually pushing the manifold 35 into position for flowing rinse water through the channels. the manifold 35, which is essentially T-shaped in crosssection, comprises a pair of elongated strip- like plugs 36 with an enlarged head 37. A continuous shoulder 38 is formed on the lower surface of the head 37. The two plugs are rigidly connected together by a pair of cross members 39 so as to form a single, integral unit.

Each of the plugs 36 is provided with a continuous, sidewise opening groove 40. An endless resilient O-ring of rubber-like band 41 is postioned in each groove 40. Thus, when the plugs 36 are manually pushed into the sockets 25, the rings 41 compress laterally and frictionally seal against their adjacent, socket wall portions 26.

The plugs 36 are not as high as the depths of their sockets. Thus, a space 43 is formed between each of the plugs and the base of their sockets. This space 43 forms a chamber for liquid.

Each manifold plug has a central opening 44. Rinse water may be flowed into the central opening 44 formed in one of the manifold plugs (see FIG. 5) so that the water flows into the space or chamber 43 in the socket. From there, the water flows simultaneously through the inlet holes 22 into the channels 18. The flow of water exits from the outlet holes 23, into the space 43 between the opposite plug and socket base, and then out through the central opening 44 in the opposite plug. The flow of the water may be facilitated by using a vacuum pump device, such as is typically found in laboratories. The liquid may be applied to the inlet plug by pouring it through a small funnel or the like, or through the action of a pump.

At times, it may be necessary to apply a second solution, such as a secondary or tracer antibody solution, for further incubating the membrane materials. This, too, can be applied through the manifold for immediate and simultaneous filling of all of the channels. Thereafter, the unbound secondary antibody materials can be washed away, using a rinse water flow, in the same manner as mentioned above.

The manifold plugs stay in place due to the resilient compression of their O-rings or bands. That same ring or band seals against the loss of liquid. The plugs are frictionally held in place, by the compressed rings, so as to avoid the need for mechanical fasteners. Thus, the manifold can be easily pulled out of the sockets, or applied, using one hand and without tools.

The manifold plugs may be made in two separate parts, without the cross-member connections so that they are handled as two separate units. This may be applicable where a single array of longer channels are used.

This invention may be further developed within the scope of the following claims.

Accordingly, having fully described an operative embodiment of this invention, I now claim:

1. An apparatus for use in blot screening solutions of antibody and the like materials by simultaneously reacting a substantial number of separated, microliter size volume samples of such material with a reactive material pattern on a paper-like membrane, comprising:

a channel plate having an inner surface and an opposite, outer surface;

an array of a substantial number of elongated, open channels formed in, and opening at, said plate inner surface, with said channels being substantially parallel, shallow in depth, narrow and closely spaced apart from each other;

elongated, narrow grooves formed in the plate outer surface and extending transversely of the channels and overlapping opposite end portions of the channels to provide a pair of depressed, approximately U-shaped in crosssection sockets, each having a base and opposite side walls and end walls;

a hole extending from each of the opposite end portions of each channel to the base of its respective overlapping socket, with each of the opposite channel holes being generally aligned along their socket bases;

at least one manifold plug formed of an elongated strip shaped to fit within and substantially fill each socket, with each of said plugs having an inner face spaced from the socket base and socket walls adapted to be frictionally sealed against the socket walls, and an opening extending from said plug inner face to its opposite face; with said plugs being removably inserted within their sockets;

whereby the channels are adapted to be covered by a paper-like membrane with the reactive material and samples of solutions to be screened are adapted to be flowed into said channels through their respective openings for reacting and, thereafter, the plugs are adapted to be inserted in respective sockets and a fluid is adapted to be flowed through one of the plug openings into its respective socket and through the hole in that socket for simultaneous introduction into all of the channels either for reactions in the channels or for flowing out through the opposite channel holes and their overlapping socket and plug opening for simultaneously flushing all of the channels.

2. The apparatus as defined in claim 1, and including an endless, rubber-like resilient, narrow band surrounding walls defining said plugs for compression against and for frictionally sealing against adjacent, overlapped socket wall portions when the plug is inserted within its socket.

3. The apparatus as defined in claim 1, and including a shallow, continuous groove formed in the surface defining a plug wall, with the band being positioned within said continuous groove for compression therein.

4. The apparatus as defined in claim 2, and including an outer manifold portion integral with the manifold plug and extending the length of the plug and being wider than the plug to form a shoulder for engaging against the plate opposite outer surface when the plug is inserted within its socket.

5. The apparatus as defined in claim 1, and including said at least one manifold plug having a cross member rigidly joining them together so that two plugs form a single, integral unit and may be inserted and removed as a unit from respective sockets.

6. A manifold system for simultaneously flowing a fluid into and out of numerous parallel, elongated, narrow, shallow channels spaced apart to form separated reaction channels that are formed in a test apparatus plate, and wherein holes extend from the channels through the plate for separately introducing fluid into each channel, comprising:

an elongated, narrow groove formed in a face of the plate remote from the channels to provide a narrow, elongated socket which transversely overlaps the channels, and with the socket having a depressed base and a continuous socket forming wall, and with holes opening into the base of the socket;

a manifold formed with an elongated plug shaped to closely fit into the socket for frictionally sealing against walls of the socket and with the plug having an inner face that is gapped from a base of the socket;

a passage formed through the manifold to its inner face for the flow of fluid through the manifold and into the socket for simultaneously introducing fluid through all of the holes opening into the socket base and thus into all of the channels.

7. The manifold system as defined in claim 6, and including a second socket-forming groove and a second manifold, each similar to the first mentioned groove and manifold, with each of the channels having a hole near each of its opposite ends for opening into one or the other of the socket bases;

whereby fluid is adapted to be continuously flowed through one of the manifolds and simultaneously through the channels and then out of the other manifold.

8. The manifold system as defined in claim 7, and including an endless, resilient, narrow band surrounding each of the walls defining said manifolds for compressing against and frictionally sealing the manifolds against the socket walls when the manifold are inserted within respective sockets.

9. The manifold system as defined in claim 8, and including a shallow, continuous, band-receiving groove formed in each manifold wall and with the band being positioned within said groove for maintaining the position of the band upon the manifolds and for sealing the manifolds against the socket walls.

10. The manifold system as defined in claim 9, and including each said manifold having an outer portion forming a continuous shoulder extending therearound for engaging against the plate outer surface defining and surrounding their respective sockets.

11. The manifold system as defined in claim 10, and including each said manifold being generally T-shaped in cross-section, said "T" having a stem and head portion with the stem portion forming a plug and the head portion forming a shoulder for engagement against the exposed plate face surrounding and defining the groove.

12. The manifold system as defined in claim 7, and including each said manifold having a cross member joining said manifolds together substantially rigidly so that the two manifolds form a single unit and may be manually inserted and removed from their respective sockets simultaneously.

13. The manifold system as defined in claim 12, and said cross member being formed of at least one narrow, rigid strip having opposite ends integral with respective manifolds for rigidly securing the manifolds together and maintaining the spacing between the manifolds.

* * * * *